United States Patent [19]

Erickson

[11] Patent Number: 5,040,526

[45] Date of Patent: Aug. 20, 1991

[54] SURGICAL DRESSING COVER

[75] Inventor: Esther Erickson, Oakville, Wash.

[73] Assignee: Cheryl Travaglione, Shelton, Wash.

[21] Appl. No.: 496,084

[22] Filed: Mar. 15, 1990

Related U.S. Application Data

[63] Continuation of Ser. No. 204,453, Jun. 9, 1988, abandoned.

[51] Int. Cl.⁵ ............................................. A61F 13/00
[52] U.S. Cl. ................................... 128/171; 128/157; 2/44
[58] Field of Search ................... 128/75, 78, 155, 157, 128/171, 335, 870; 2/44; 450/2, 96

[56] References Cited

U.S. PATENT DOCUMENTS

| | | | |
|---|---|---|---|
| 1,995,002 | 3/1935 | Lee | 128/78 |
| 2,717,437 | 9/1955 | DeMestral | 2/235 |
| 3,068,860 | 12/1962 | Strazdas | 128/78 |
| 3,194,234 | 7/1965 | Duckman et al. | 128/155 |
| 3,417,749 | 12/1968 | Bailey | 128/171 |
| 3,442,270 | 5/1969 | Steinman | 128/157 |
| 3,561,442 | 2/1971 | Goswitz | 128/157 |
| 4,825,866 | 5/1989 | Pierce | 128/335 |

FOREIGN PATENT DOCUMENTS

| | | | |
|---|---|---|---|
| 0730924 | 3/1966 | Canada | 128/335 |
| 2268504 | 11/1975 | France | 128/335 |

Primary Examiner—Randall L. Green
Assistant Examiner—Paul Prebilic
Attorney, Agent, or Firm—Robert W. Beach; Ward Brown

[57] ABSTRACT

A back compression dressing has two cooperating flexible sheet components, each of such components having a body-bonding adhesive-backed section and an elongated flap section joined in edge relationship and the flap sections having cooperating hook-and-pile fastener strip components, respectively, arranged for interengagement to hold the flaps in overlapping relationship when the body-bonding portions of the components are bonded to a patient's body at opposite sides of the lumbar region of the back.

3 Claims, 2 Drawing Sheets

SURGICAL DRESSING COVER

This is a continuation of co-pending application Ser. No. 07/204,453 filed on June 9, 1988 now abandoned.

BACKGROUND OF THE INVENTION

1. Field of the Invention

This invention relates to a compression dressing for covering a spinal portion of a patient's back.

2. Prior Art

The Strazdas U.S. Pat. No. 3,068,860, issued Dec. 18, 1962, discloses a back plaster for exerting pressure upon the spinal column in the lumbar region and could be used to overlie a dressing applied to a spinal portion of the back following surgery. The plaster is roughly cross shaped and four flaps arranged orthogonally carry adhesive coating which is bonded to the person's body by being pressed in place. The base panel is continuous so that, if the plaster were used to hold a dressing against the patient's back, it would be necessary to strip off the back at least two of the adhesive flaps in order to provide access for changing the dressing. Such procedure can be very painful and can be increasingly painful when it is necessary to repeat the procedure.

The Lee U.S. Pat. No. 1,995,002, issued Mar. 19, 1935, discloses a compression supporting device in the form of a band including oppositely extending flaps having adhesive surfaces that can be pressed against the body to bond them to the body. The adjacent end portions of such flaps do not have adhesive on them and have rows of eyelets along their adjacent edges through which a suitable lacing can extend in crisscross fashion to draw the adjacent end portions of the flaps toward each other until the desired pressure is exerted on the body and the hips are drawn backwardly so as to compress the iliac bones into the sacrum. This device is not intended to hold a compression dressing in place.

The Goswitz U.S. patent No. 3,561,442, issued Feb. 9, 1971 discloses a mastectomy compression bandage including a body band having an elastic section to cover the portion of the chest on which the operation has been performed and a nonelastic section carrying a brassiere cup. The ends of the body band are secured together at the back by hook-and-pile fasteners, and the free end of the shoulder strap is secured to an edge portion of the elastic section by a hook-and-pile fastener. The elastic section is intended to hold a mastectomy dressing in place without the use of adhesive tape. No portion of the body band is intended to be bonded to the body by adhesive. This device would not be suitable for holding a compression bandage to the lumbar portion of the back.

A conventional bandage for holding a dressing against the lumbar portion of the back is known as a MONTGOMERY STRAP. Such MONTOGOMERY STRAP is generally of the type shown in the U.S. Lee patent No. 1,995,002 discussed above, except that the flaps do not have as great a circumferential extent and have a greater extent heightwise of the back. The sheet material is silk cloth. Instead of the adjacent edge portions of the opposite flaps being connected by a continuous lacing in crisscross fashion, the two eyelets of each pair are connected by a single tie so that the row of ties also has a row of knots extending heightwise of the back and substantially overlying the spine of the lumbar region of the back which causes discomfort to the patient lying on the bandage.

SUMMARY OF THE INVENTION

It is a principal object of the present invention to provide a compression dressing for application to the lumbar region of the back which will not produce discomfort to a patient lying on the back.

Another object is to provide a back compression dressing which is easy to apply and which will hold securely.

A further object is to provide a body band of a compression dressing that can be manipulated quickly, easily and painlessly for enabling the pad of the dressing to be replaced.

The foregoing objects can be accomplished by a compression dressing including a body band composed of two sheet sections having adhesive-backed portions and flaps that are not adhesive-backed, which band components can be bonded to the back of a patient at opposite sides of the lumbar region with the nonadhesive flaps disposed in adjacent relationship capable of being overlapped and the edge portions of such flaps having cooperating hook-and-pile fasteners that can secure the flaps together over a dressing pad.

DETAILED DESCRIPTION

The back compression dressing includes two flexible sheet body band components 1 that can be made of strong flexible fabric, preferably silk cloth. Each of these components includes two principal sections, namely, a body-bonding section having an adhesive back 2 bearing adhesive suitable for bonding to a patient's body and a flap section 3A or 3B which has a nonadhesive back. The sections of each component are joined in edge relationship to form a hinge line or folding area 4 therebetween.

The body band components are elongated lengthwise of the hinge lines 4 so that the sheets will extend a greater distance heightwise of the back than circumferentially of the body. Such proportions will enable the body band components of the compression dressing to retain a dressing pad along a desired heightwise portion of the back while providing adequate bonding of the body band components to the body. The dressing may, however, be cut with scissors to provide a dressing of lesser height if desired.

Figure 2:
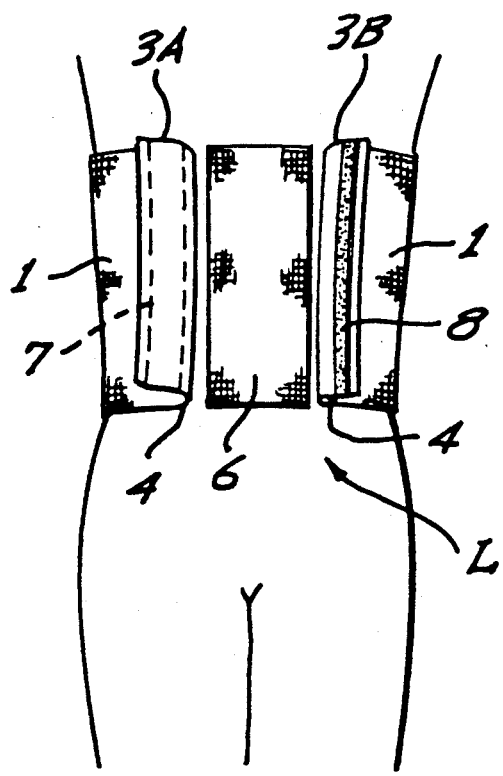
FIG. 2 is a plan of the compression dressing illustrating an intermediate step in its application to the body and FIG. 3 is a similar view illustrating the application of the compression dressing to the body as having been almost completed.
Figure 1:
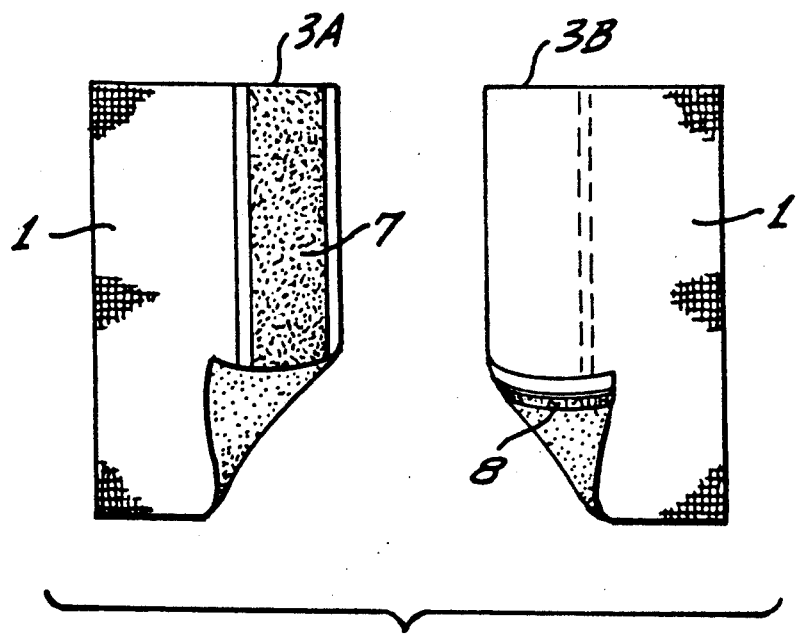
FIG. 1 is a plan of two cooperating components of the compression dressing prior to being applied to the body.

FIG. 1, which shows the sheet components of the compression dressing before being applied to the body, illustrates slick liners 5 applied over the adhesive backing 2 to protect the adhesive prior to use. Such liners can be stripped off easily and quickly when it is desired to apply the sheet components to the body. When such protective liners have been removed, the two sheet components of the compression dressing can be applied to circumferentially opposite sides of the lumbar portion of the back with their flaps 3A and 3B turned back away from each other about the hinge lines 4, as shown in FIG. 2. The adhesive sections of such sheet components should be spaced apart sufficiently in applying them to the body to provide an adequate space between their adjacent edges to receive a dressing pad 6 between them, but close enough together to enable the flaps 3A and 3B to overlap considerably. Such space can therefore be covered by the cooperating flaps 3A and 3B.

Figure 3:
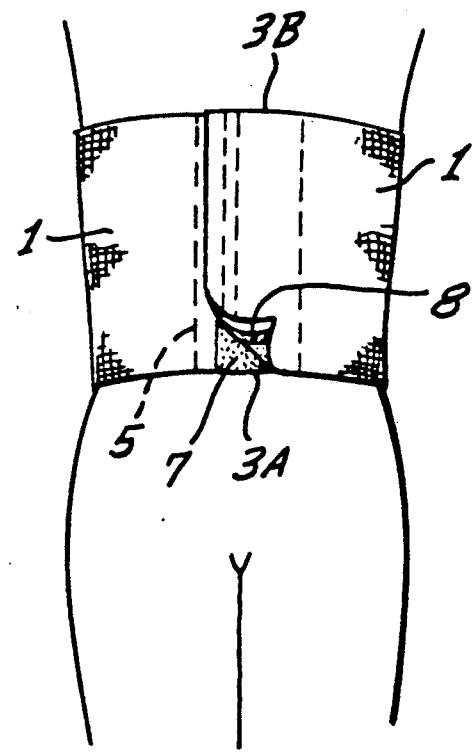
Figure 4:
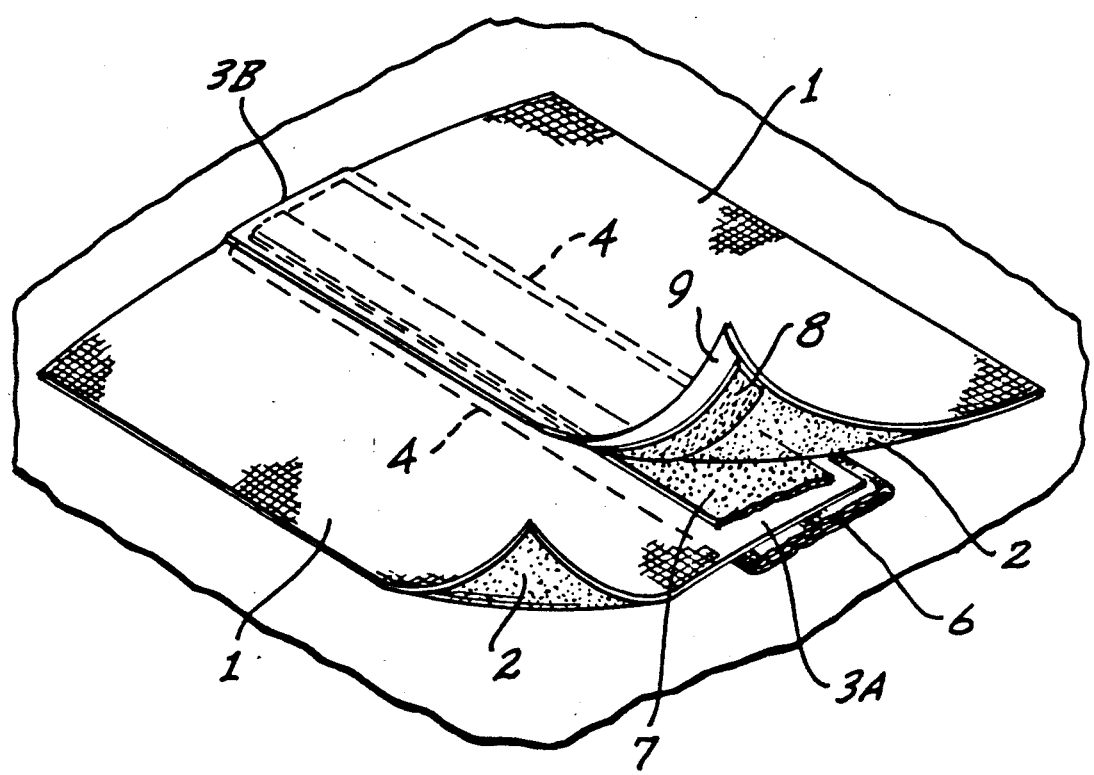
FIG. 4 is a top perspective of the compression dressing on an enlarged scale substantially as applied to the body but with portions turned up to reveal features of the compression dressing.

Flap 3A is the underflap or underlapping flap which will be folded relative to the body-bonding section 1 about the hinge line 5 from the position of FIG. 2 downward into a position directly overlying the dressing pad 6 to the position shown in FIG. 3. The surface of such flap facing the body is coated with a layer of air and liquid impervious plastic material to overlie, the dressing. Next, the overflap or overlapping flap 3B will be folded over the underflap or underlapping flap 3A and the dressing pad 6, as shown in FIGS. 3 and 4 and, similarly, has an underlayer of plastic.

The flaps 3A and 3B are held in their overlapping relationship by coacting elongated strip components of a hook-and-pile fastener. The outer side of the underflap 3A opposite the adhesive side of the body-bonding section 1 has bonded to it a hook-and-pile fastener strip component 7 which may be of pile fabric and the underside of overflap 3B on the same side as the adhesive of the body-bonding section joined to it has bonded to it a hook-and-pile strip component of hook fabric 8. These hook-and-pile fastener strip components extend generally parallel to the edges of the flaps so that, as the overlapping flap 3B is folded down over the underlapping flap 3A, the hook strip component 8 of the hook-and-pile fastener will grip the strip pile fabric component 7 to deter separation of the hook-and-pile components and virtually to prevent movement of the sheet components of the compression dressing edgewise away from each other circumferentially of the body.

Preferably, the hook strip 8 of the hook-and-pile fastener on the underside of the overflap 3B is spaced from the adjacent edge of that flap remote from the body-handing section to provide a lip 9 that can be grasped and pulled to separate the hook component of the fastener from the pile component of the fastener easily. Also, it is preferred that the pile component 7 of the fastener on the underlapping flap 3A be of a width greater than the width of the hook component 8 of the fastener on the overlapping flap 3B circumferentially of the body so that the spacing between the hinge lines 5 of the sheet components of the compression dressing can be selected to provide spaces of different widths between the adjacent edges of the sheet components for reception of dressing pads 6 of different widths and to provide the same area of cooperating engagement between the hook component and the pile component of the fastener to provide the same amount of grapping actions without the location of the sheet components 1 on the body being critical.

When the adhesive-backed sections of the sheet components 1 of the compression dressing have been pressed firmly against portions of the back at opposite sides of the lumbar region L of the spinal column in desired positions, the compression dressing pad 6 can be laid between the spaced hinge lines of the two sheet components as shown in FIG. 6. Then the underflap or underlapping flap 3A can be folded over the dressing pad followed by folding the overflap or overlapping flap 3B over the underflap or underlapping flap 3A and pressing it against the underlapping flap to secure the hook strip component 8 of the fastener to the pile strip component of the fastener with the flaps drawn sufficiently taut circumferentially of the body to hold the dressing pad 6 securely in position with the desired amount of pressure against the back.

When it is desired to change the dressing pad 6, it is only necessary to grasp the lip 9 of the overflap 3B and lift it to strip the hook strip component 8 of the hook-and-pile fastener from the pile strip component 7 of such fastener. The overflap 3B can then be folded away from the space between the adjacent edges of the sheet components of the compression dressing about its hinge line 4 followed by folding back the underflap 3A about its hinge line 4 to expose the dressing pad 6 for replacement.

I claim:

1. A surgical dressing cover for application to a body comprising two cooperating flexible sheet band components, each of said sheet band components having a body-bonding adhesive -backed section and a dressing-covering flap section joined integrally to said body-bonding section in edge relationship along one edge of said body-bonding section, said body-bonding adhesive-backed section being adapted to be bonded to the body with adjacent edges in spaced relationship, said flap section of one of said sheet band components being an underlapping flap section and having on its face opposite the adhesive back of the body-bonding section joined integrally thereto one fastening component of a hook-and-pile fastener and said flap section of the other of said sheet band components being an overlapping flap section having on its face on the same side as the adhesive backing of the body-bonding section joined integrally thereto the other fastening component of said hook-and-pile fastener for cooperative interengagmenet of said two fastening components when securing said two dressing-covering flap sections in overlapping relationship with said overlapping flap section covering said underlapping flap section in the space between the adjacent hedges of said body-bonding sections when bonded to the body thereby enabling said overlapped flap sections to confine a surgical dressing disposed between said body-bonding adhesive-caked sections, each fastening component of said hook-and-pile fastener extending substantially the full length of the adjacent edge of its body-bonding adhesive-backed section and the width of the fastening component of the hook-and-pile fastener on one flap section being narrower transversely of the adjacent edge of its body-bonding adhesive-backed section than he width of the fastening component on the other flap section transversely of the adjacent edge of its body-bonding adhesive-backed section to provide the same holding action of the hook-and-pile fastener for different spacings of said body-bonding adhesive backed sections.

2. The surgical dressing cover defined in claim 1, in which at least one fastening component of the hook-and-pile fastener is a strip extending along a flap section edge parallel to the edge of the body-bonding section to which such flap section is joined for a distance substantially equal to the length of said flap section edge.

3. The surgical dressing cover defined in claim 1, in which the fastening component of the hook-and-pile fastener on the overlapping flap section is spaced from the edge of such overlapping flap section remote from its body-bonding adhesive-backed section for forming a lip that can be grasped for pulling the overlapping flap fastening component away from the underlapping flap fastening component.

* * * * *

UNITED STATES PATENT AND TRADEMARK OFFICE
CERTIFICATE OF CORRECTION

PATENT NO.  : 5,040,526
DATED       : August 20, 1991
INVENTOR(S) : Esther ERICKSON It is certified that error appears in the above-identified patent and that said Letters Patent is hereby corrected as shown below:

Claim 1: Column 4, line 23, change "section" to --sections--; line 33, cancel "interengagmenet" and insert --interengagement--; line 38, cancel "hedges" and insert --edges--; line 41, cancel "adhesive-caked" and insert --adhesive-backed--; line 48, cancel "he" and insert --the--.

Signed and Sealed this

Third Day of November, 1992

Attest:

DOUGLAS B. COMER

*Attesting Officer*    *Acting Commissioner of Patents and Trademarks*